US012629225B2

(12) United States Patent
Fischer et al.

(10) Patent No.: US 12,629,225 B2
(45) Date of Patent: May 19, 2026

(54) EXTRACORPOREALLY LENGTH-ADJUSTABLE IMPLANT SYSTEM, AND LENGTH-ADJUSTABLE IMPLANT COMPONENT

(71) Applicant: WALDEMAR LINK GmbH &Co. KG, Hamburg (DE)

(72) Inventors: Hans-Joachim Fischer, Norderstedt (DE); Helmut D. Link, Hamburg (DE); Klaus Dmuschewsky, Hamburg (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 944 days.

(21) Appl. No.: 17/904,710

(22) PCT Filed: Feb. 24, 2021

(86) PCT No.: PCT/EP2021/054500
§ 371 (c)(1),
(2) Date: Aug. 19, 2022

(87) PCT Pub. No.: WO2021/170612
PCT Pub. Date: Sep. 2, 2021

(65) Prior Publication Data
US 2023/0109975 A1 Apr. 13, 2023

(30) Foreign Application Priority Data
Feb. 25, 2020 (EP) ..................................... 20159426

(51) Int. Cl.
*A61B 34/00* (2016.01)
*A61B 17/72* (2006.01)
(Continued)

(52) U.S. Cl.
CPC .......... *A61B 34/73* (2016.02); *A61B 17/7216* (2013.01); *A61F 2/28* (2013.01);
(Continued)

(58) Field of Classification Search
CPC . A61B 34/73; A61B 17/7216; A61B 17/7016; A61B 2017/00991
See application file for complete search history.

(56) References Cited

U.S. PATENT DOCUMENTS

| 7,753,915 B1 | 7/2010 | Eksler et al. |
| 2004/0030395 A1 | 2/2004 | Blunn et al. |
| | (Continued) | |

FOREIGN PATENT DOCUMENTS

| CN | 102895048 A | 1/2013 |
| EP | 1611868 A2 | 1/2006 |

OTHER PUBLICATIONS

International Search Report and Written Opinion mailed Sep. 7, 2021, in connection with International Patent Application No. PCT/EP2021/054500, filed Feb. 24, 2021, 17 pgs. (including translation).

*Primary Examiner* — Brian A Dukert
(74) *Attorney, Agent, or Firm* — WALDEMAR LINK GMBH & CO. KG

(57) ABSTRACT

An extracorporeally length-adjustable implant system comprises an implant component to be fastened to a bone to be lengthened and an adjustment device with two fastening parts that are displaceable relative to one another, each of which is intended for arrangement at a part of the bone to be lengthened, wherein the adjustment device is able to distract the two fastening parts and comprises a drive element with a permanent magnet arranged in rotationally fashion and a mechanism which converts a rotational movement of the permanent magnet into a distracting longitudinal movement of the adjustment device; and an extracorporeal drive unit for the drive element of the implant component. The extracorporeal drive unit comprises a rotatably mounted extracorporeal magnetic ring with an interior to receive the bone (Continued)

to be lengthened with the adjustment device, and an actuation device to rotate the extracorporeal magnetic ring in the ring plane thereof.

19 Claims, 10 Drawing Sheets

(51) Int. Cl.

| | |
|---|---|
| *A61F 2/28* | (2006.01) |
| *A61B 17/00* | (2006.01) |
| *A61B 17/68* | (2006.01) |
| *A61F 2/30* | (2006.01) |
| *A61F 2/46* | (2006.01) |

(52) U.S. Cl.
CPC ............... *A61B 2017/00411* (2013.01); *A61B 2017/681* (2013.01); *A61F 2002/2825* (2013.01); *A61F 2002/3055* (2013.01); *A61F 2002/30601* (2013.01); *A61F 2002/30668* (2013.01); *A61F 2002/30706* (2013.01); *A61F 2002/4698* (2013.01)

(56) References Cited

U.S. PATENT DOCUMENTS

| | | |
|---|---|---|
| 2011/0230883 A1 | 9/2011 | Zahrly et al. |
| 2017/0049489 A1 | 2/2017 | Pool |

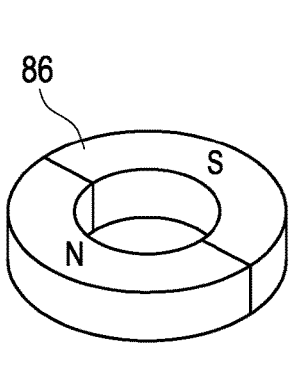
Fig. 3 a
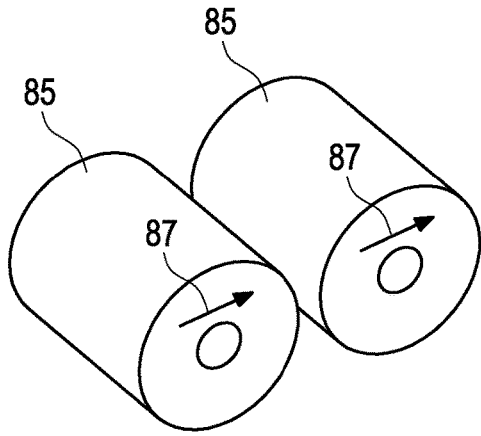
Fig. 3 b
Fig. 4

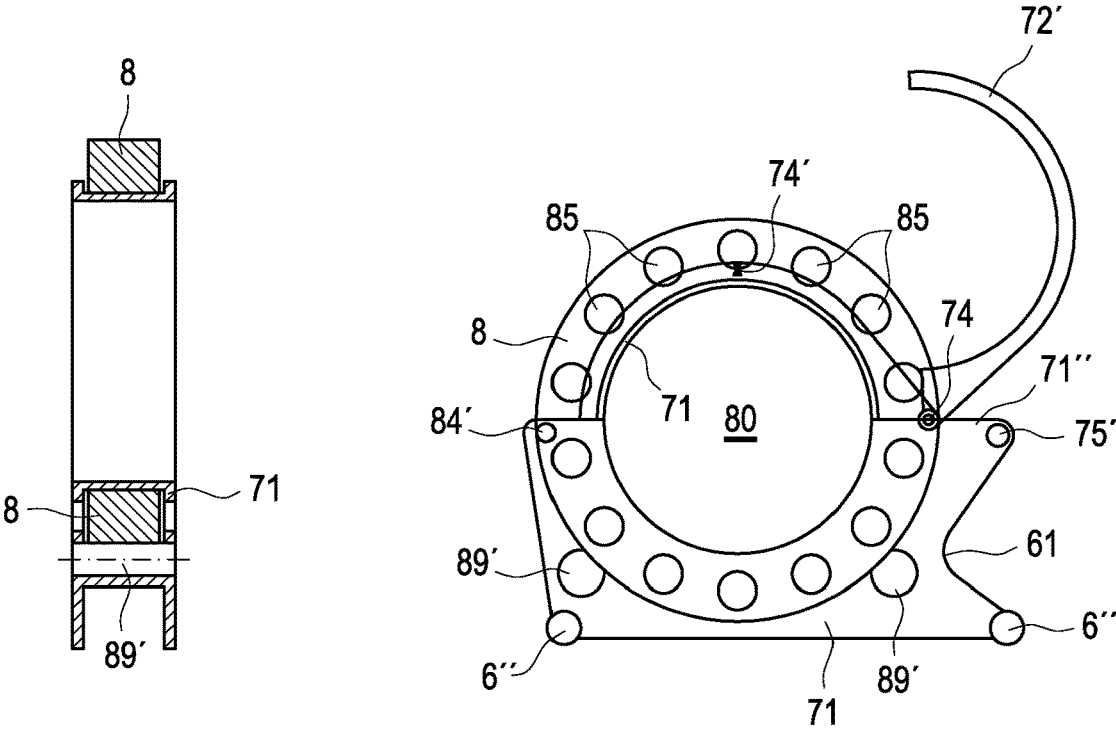
Fig. 13 a                    Fig. 13 b
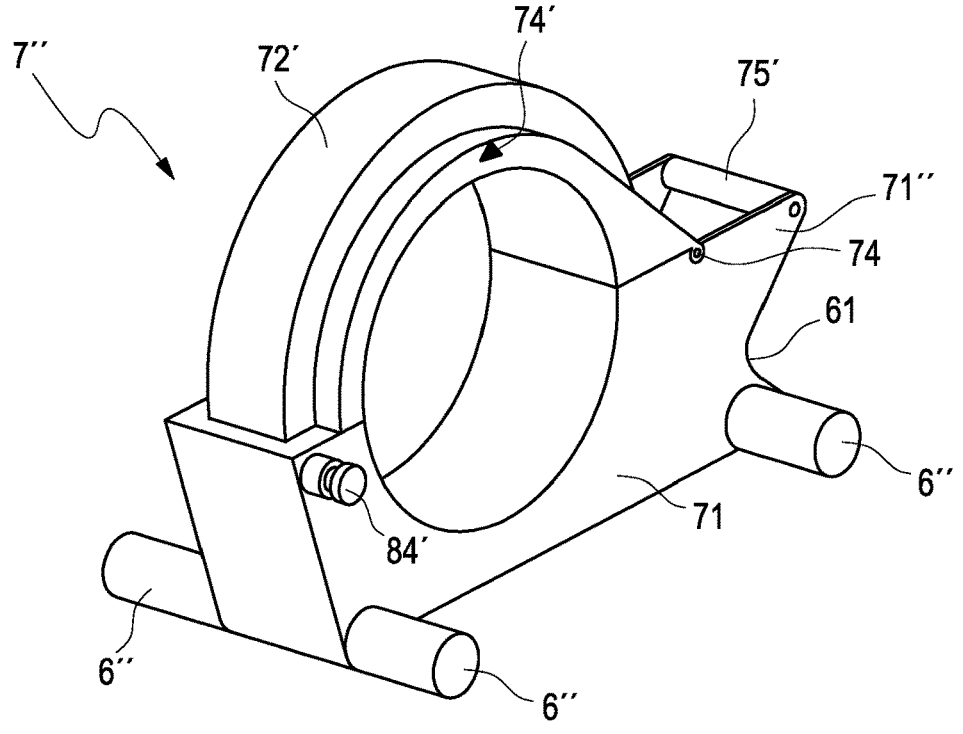
Fig. 14

EXTRACORPOREALLY LENGTH-ADJUSTABLE IMPLANT SYSTEM, AND LENGTH-ADJUSTABLE IMPLANT COMPONENT

CROSS REFERENCE TO RELAETD APPLICATIONS

This application is a National Stage application under 35 U.S.C. 371 of International Patent Application No. PCT/EP2021/054500, filed Feb. 24, 2021, which claims priority to European Patent Application No. 20159426.4, filed Feb. 25, 2020, the disclosures of all are incorporated herein by reference in their entirety.

FIELD

The invention relates to a system which can be adjusted from the outside (extracorporeally) for adjusting the length of an implant component as part of an endoprosthesis and to an adjustment device therefor. The adjustment device is provided for a prosthesis shaft of the implant component, which is designed for fastening to a bone to be lengthened, and comprises fastening parts that are displaceable relative to one another, each of which is to be arranged on a part of the bone to be lengthened, and an adjustment element driven by a drive element, which is designed to displace the two fastening parts that are displaceable relative to one another.

BACKGROUND

Intracorporeally adjustable prostheses have significance for applications in which prostheses are to grow along, so to speak. They are indicated in particular in such cases where a correspondingly longer prosthesis is required either on account of natural processes, for example during the growth of children, but also for such applications in which the bone is gradually stretched along a separation or breaking point for bone formation (osteogenesis) in order to continuously stimulate the formation of new cells. For example, in the latter application, the two bone parts formed by the separation point are successively moved away from one another, for example by 1 mm per day, in order to constantly stimulate the formation of new bone tissue. In this way, for example, an extremity, such as a leg, can be lengthened. This is important in order to produce a length compensation between the two legs of a person. In a similar manner, albeit generally more slowly, it is also possible to achieve through constantly increasing the length of a prosthesis that the bone that is supplied with the prosthesis becomes longer in a manner similar to that of the natural growth process of children or adolescents.

It has been known for a long time that external fixatives are used for such cases. However, these have serious disadvantages, for example they are unmanageable and risk accidents, and moreover, they have a high risk of infections.

In order to counteract these disadvantages, implantable prostheses have been developed which enable a desired length adjustment by means of an intracorporeally implanted prosthesis. In this case, the actual length adjustment can take place invasively, in particular in the case of a purely mechanical length adjustment, or by means of a drive which is implanted on the prosthesis and is remotely controlled from the outside (Mutars System of the German company lmplantcast GmbH, Synoste System of the Finnish company Synosts Oy).

The latter offer the advantage that the adjustment can be carried out from the outside in a non-invasive manner. For this purpose, the prosthesis contains an electric motor or forms a part of an electric motor which can be controlled from outside (extracorporeally). If necessary, it can also be supplied with energy from outside. Thus, such a structure comprising a so-called distributed electric motor is known, in which the prosthesis and its adjustment element form part of an electric motor (so-to-speak the rotor), and the other part with the excitation (so-to-speak the stator) is formed by an extracorporeal attachment (WO 01/786141). The actual electric motor is therefore basically arranged partially intracorporeally (with its rotor) and partially extracorporeally (with its stator).

Such an electric motor-based system is easy to operate, but incorrect operation is also relatively easy. A sufficient extracorporeal adjustability can thus be achieved, but because of the risk of an operating error, wherein the electric motor with a large adjusting force causes an incorrect adjustment that is dangerous to the patient, expert personnel is required for operation. The approval of such a system is therefore complicated and difficult. Application can usually only take place by specialist personnel, which causes additional effort. This results in coordination problems with respect to the required appointment times at which the specialist personnel has time for the (outpatient) treatment or leads to (excessively) large adjustment units (in cm of adjustment path per appointment) in order to minimize the number of visits of the patient (even at the price of possibly medically questionably large adjustment units per appointment).

SUMMARY

The object of the invention is to provide an improved system which allows extracorporeal actuation and is easier to handle.

The solution according to the invention is found in the features of the independent claims. Advantageous developments are the subject matter of the dependent claims.

In the case of an extracorporeally length-adjustable implant system comprising:

an implant component for an implantable prosthesis, which is designed for fastening to a bone to be lengthened and has an adjustment device with two fastening parts that are displaceable relative to one another, each of which is to be arranged on a part of the bone to be lengthened, wherein the adjustment device is designed to displace the two fastening parts that are displaceable relative to one another, and comprises a drive element with a permanent magnet arranged in a rotationally movable manner and a gearing mechanism which converts a rotational movement of the permanent magnet into a displacing longitudinal movement of the adjustment device; and an extracorporeal drive unit for the drive element of the implant component, it is provided according to the invention that the extracorporeal drive unit comprises a rotatably mounted extracorporeal magnet ring with an interior, which is designed to receive the bone to be lengthened with the adjustment device, and an actuation device which is designed to rotate the extracorporeal magnet ring in its ring plane, wherein the extracorporeal magnet ring is designed as a permanent magnet structure and has in its interior a directed static magnetic field, which is stationary with respect to the ring, and the extracorporeal magnet ring is mechanically rotated by the actuation device.

First, some terms used are explained:

The term "stationary with respect to the ring" is understood to mean an arrangement which is fixed in relation to the ring and co-rotates with the ring.

The term "directed" is understood to mean a typically uniform alignment of a magnetic field. In particular, the orientation of the magnetic field should have the same direction at any point in the field.

The term "homogeneous" refers to a substantially uniform magnetic field in which local deviations of the field strength in a central region comprising at least 80% of the overall region are at most +1-10% of the average value.

The term "static" is understood to mean a magnetic field of constant strength. It thus forms in particular a contrast to the typically rapidly changing electromagnetic fields.

The invention is based on the idea of departing from the concept actuated by electric motor and instead providing a mechanical actuation. The invention achieves this by providing a static magnetic field by means of the magnet ring, which magnetic field can be rotated mechanically (manually or by motor). Preferably, the magnet ring is rotated as a whole by the actuation device. The permanent magnet acting as a drive element within the implant component always aligns itself according to the static magnetic field of the magnet ring. The position of the permanent magnet acting as a drive element within the adjustment device thus results from the position or the performed rotation of the static magnetic field. With the transition to a mechanically rotated static magnetic field, the invention achieves a significant simplification and a precise position control over the position of the permanent magnet acting as a drive element. A simple manual actuation can thus suffice; current for actuation is no longer required.

This also eliminates any risk of electric shock due to a malfunction. Furthermore, any risk that a passing through or breaking away of the position adjustment can be caused by a malfunction can also be omitted, which can lead to an excessively large adjustment and thus to an injury to the bone itself and in particular to its surrounding soft parts, such as muscles or tendons. Moreover, due to the constant static magnetic field, a load on the patient by eddy currents, as generated by changing electromagnetic fields, is avoided.

The system according to the invention with its drive unit based on the static magnetic field can thus also be operated by assistants or laypersons, basically also by the patient itself. In medical practice, this represents a considerable advantage since the patient can thus actuate the adjustment device at home if necessary. It is thus possible to carry out the adjustment more frequently and then in gentler shorter sections than was previously possible in the prior art, in particular if operation could only take place by trained specialist personnel.

Furthermore, the invention allows a precise control of the alignment of the static magnetic field with the rotatable magnet ring. A fine adjustment of the angular position of the drive element of the adjustment device can thus be achieved, which enables a very precise setting of the adjustment performed.

In this way, the invention achieves an increase in the adjustment safety in a surprisingly simple manner while simplifying the drive unit at the same time, which thus renders it suitable for laypersons and patients.

Preferably, the magnet ring can be divided into at least two segments in order to thus create an openable and closable access to the interior of the magnet ring for a body part, in particular a leg or arm, provided with the prosthesis shaft. The magnet ring and thus the drive unit as a whole can thus be arranged in a simple manner at the location at which the implant component comprising the adjustment device is arranged in the body. For example, the drive unit can be easily positioned in the region of the thigh of a patient by unfolding the magnet ring, in order to adjust the implant component arranged in the shaft of a in the femur. A threading through of the extremity to be treated by the magnet ring is thereby omitted. The rest of the drive unit is preferably designed in such a way that free access to the interior thereof is made possible with the unfolding of the magnet ring. The application is thus considerably easier thanks to the unfoldable magnet ring.

It is also expediently provided that the unfolding of the magnet ring by the magnetic force of the magnets arranged in the magnet ring is neither prevented nor promoted. For this purpose, the magnet ring is designed such that it can be unfolded without magnetic force. The term "without magnetic force" is understood here to mean that the force directed against unfolding by the magnetic force is either zero or so small that an operator can easily overcome it manually, in particular without the addition of tools. For this purpose, a separation plane between the segments is advantageously selected such that it extends in the direction of the directed static magnetic field. It is thus achieved that portions of the magnetic force running transversely to the separation plane are minimized.

In this case, the segments are preferably connected to connecting means, of which at least one is openable and reclosable and at least one is foldable in a hinge-like manner. Thanks to these connecting means, the segments can be easily opened and after placing the relevant extremity (that body part in which the implant component is contained with the adjustment device according to the invention, in particular an arm or a leg) can be closed again. In the one of the connecting means, a hinge-like folding capability makes it possible to avoid complete removal of the openable segment (although the latter would also be possible in principle). Handling is thus further facilitated.

In the opened, unfolded state, the magnet ring is preferably secured against (undesired) movement. To this end, a locking device is expediently provided, which fixes the magnet ring with its segments in the open position in a torsion-proof manner. Thus, the risk of unplanned movement of the magnet ring, which could also lead to undesired folding, is counteracted in an effective manner. Furthermore preferably, a securing device is provided in the reverse sense, which securing device is designed in particular by means of a positive guidance to bring about a coupling of the magnet ring in the closed position. An unfolding of the magnet ring out of the open position is thus blocked. This reliably prevents undesired opening of the magnet ring, for example during normal actuation.

The magnet ring is designed with permanent magnets. It is expediently formed by means of a plurality of sub-magnets which are arranged on the magnet ring. This makes it possible to use commercially available and thus cost-effectively available typical permanent magnets as sub-magnets. Thus, relatively large magnet rings can also be produced efficiently and with relatively little weight. The individual sub-magnets, individual magnets, are preferably similar, namely in particular designed as magnetic dipole bodies, preferably made of rare earth metals (so-called rare earth magnets).

In this case, the sub-magnets are preferably used with different field orientation in an angularly fixed manner at regular intervals along the magnet ring. Due to the angularly fixed arrangement, the sub-magnets in the magnet ring always maintain their field orientation. By using the individual sub-magnets with different field orientation, it is possible to create such a field profile of the static magnetic field that the result is a field concentration inside the magnet ring and a field extinction outside the magnet ring. Furthermore, it is possible in this way to generate a homogeneous magnetic field within the magnet ring. Ideally, this is achieved by as many and as small sub-magnets as possible, but a good approximation for a virtually homogeneous field in the magnet ring can already be achieved with a number of sub-magnets of about a dozen (10 to 20).

Furthermore, the sub-magnets are expediently arranged in such a way that their magnetic field (more precisely, the stray fields outside of the sub-magnets) is maximally compensated in each case along a separation plane between segments of the magnet ring. The magnetic field transverse to the separation plane can thus be minimized. This is a particularly advantageous way of achieving in a simple and reliable manner that the segments can be opened without magnetic force, as already explained above.

Advantageously, a housing which surrounds the magnet ring is provided for the drive unit. With the housing, magnetic fields outside the magnet ring, in particular stray fields, are short-circuited so that the exterior space surrounding the housing is largely free of magnetic fields ("external field-free"). For this purpose, the housing has one or more shields and/or is preferably formed from soft magnetic material. This results in no influence on the outside by the magnetic field of the magnet ring (which is quite strong in the interior). Reliable transport is thus significantly facilitated.

The drive unit is expediently provided with a positioning device which acts on the magnet ring, in particular a counting mechanism indicating revolutions of the magnet ring. This allows the position of the magnet ring to be indicated, allowing the user to make a fine and accurate adjustment. This applies both to the angular position of the magnet ring and to the number of revolutions of the magnet ring. For example, information about the adjustment path of the adjustment device which has been brought about with the drive device, can be indicated to the operator by means of a counting mechanism in a readable and reproducible manner.

Advantageously, an extracorporeal blocking switch can also be provided, which is preferably arranged on the drive unit and acts on an adjustment-blocking member arranged on the prosthesis shaft. The adjustment element of the implant component can thus be blocked against unintentional adjustment by means of the adjustment-blocking member. If an adjustment with the drive unit is provided, the adjustment-blocking member is released by means of the blocking switch, and the adjustment element is thus released again in order to thus be able to carry out the desired adjustment by means of the drive unit.

The drive unit is preferably provided with a supporting foot. It holds the drive unit in an upright position and at the same time functions as a tilting protection in order to thus keep a correct relative positioning of the drive unit to the implant component. In order to achieve an initial correct positioning, the supporting foot is preferably furthermore provided with a direction-oriented receptacle for the body part, in particular arm or leg, into which the implant component comprising the adjustment device is implanted.

The invention also extends to the extracorporeal drive unit as such as described above for the system.

The invention furthermore extends to the implant component comprising the adjustment device as such as described above for the system. In particular, the invention also extends to such an implant component in which the adjustment device is designed such that a drive element with a permanent magnet arranged rotationally movably acts via a gearing mechanism on a spindle drive for converting a rotational movement of the permanent magnet into a displacing longitudinal movement, wherein the drive element is designed for actuation by means of a magnetic field of an extracorporeal drive unit, and is provided particularly advantageously with a bending beam for transmitting power from the drive element to the spindle drive.

Thanks to the bending beam, which is elongated and designed to absorb or transmit shear forces, a bending of the implant component that arises under load can be compensated. The bending beam makes it possible to compensate for an angle error between the drive element with the gearing mechanism (reduction gear) on the one hand and the actual spindle drive on the other hand. Such an angle error arises in particular in that the implant component bends under high load. The fastening parts moving relative to one another, typically inner and outer tubes of a telescopic adjusting mechanism, are bent under load transversely to their central axis. There is then the risk that with respect to its axis, the actual drive element comprising the gearing mechanism is no longer aligned exactly with the axis of the spindle drive. Such misalignments, which are usually only based on small angular differences, can lead to a blocking of the mechanism. The invention has recognized that this can be reliably prevented in a surprisingly simple manner by means of a bending beam between the drive element and the gearing mechanism on the one hand and the spindle drive on the other hand. Thus, even under high load, there is no risk of the adjustment element being blocked.

For this purpose, the drive spindle expediently has a central bore which is open on one side and into which the bending beam is inserted. The bending beam is thus guided well on the one hand, and, on the other hand, a relatively large length for the bending beam results in a compact construction. This makes it possible to absorb even relatively large angle errors of up to about +/−5 degrees by means of the bending beam. For the force-fitting connection between the bending beam on the one hand and the drive spindle on the other hand, a coupling between the free end of the bending beam and the drive spindle is preferably provided at the bottom of the central bore. For this purpose, it is furthermore expediently provided that the bending beam has a length which preferably corresponds to at least one third, more preferably at least one half, of the length of the drive spindle, and in particular is designed to absorb an angular offset of up to +/−5 degrees. Advantageously, the bending beam is designed to be laterally constricted along its main part. On the one hand, this facilitates the desired bending of the bending beam and, on the other hand, ensures the required clearance of the bending beam in the central bore.

For further details on the interaction of the implant component with the drive device, reference is made to the above description.

BRIEF DESCRIPTION OF THE DRAWINGS

The invention is explained in more detail below with reference to the attached drawing using advantageous embodiments. In the drawings:

FIGS. 3a, b are schematic representations of a sub-magnet and physical representation of two sub-magnets arranged adjacently;

FIG. 4 is a front view of a first embodiment of a drive unit comprising a magnet ring according to the present invention;

FIGS. 13a, b are a front and a side view of a third embodiment with a pivotable protective cover;

FIG. 14 is a perspective view of the third embodiment;

DETAILED DESCRIPTION

Figure 1:
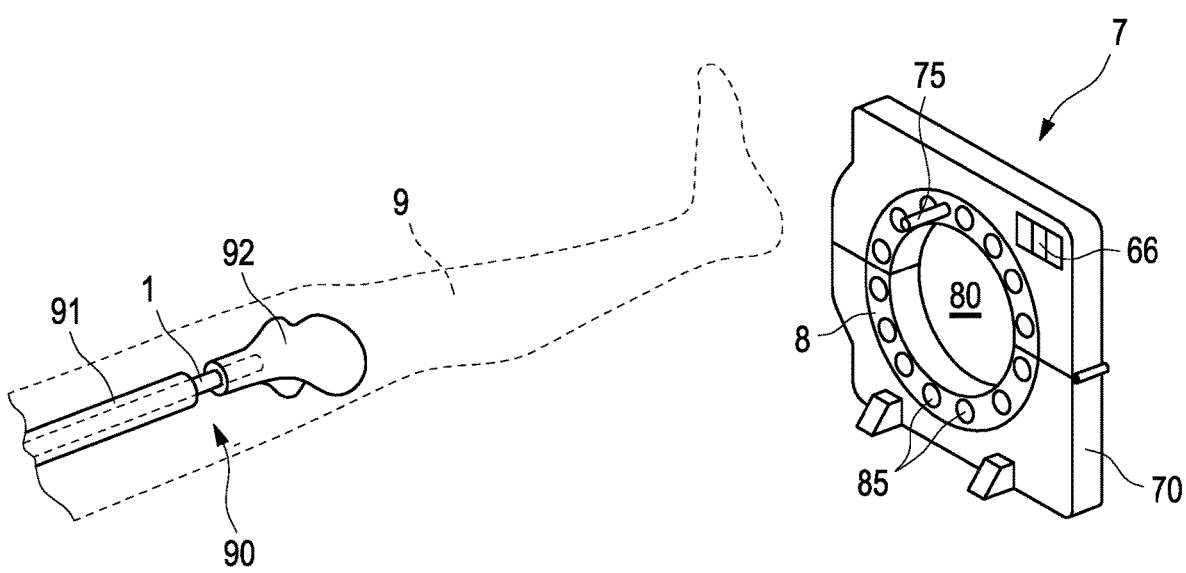
FIG. 1 is a schematic view of a bone with inserted implant component and a drive unit arranged next to it.
Figure 16:
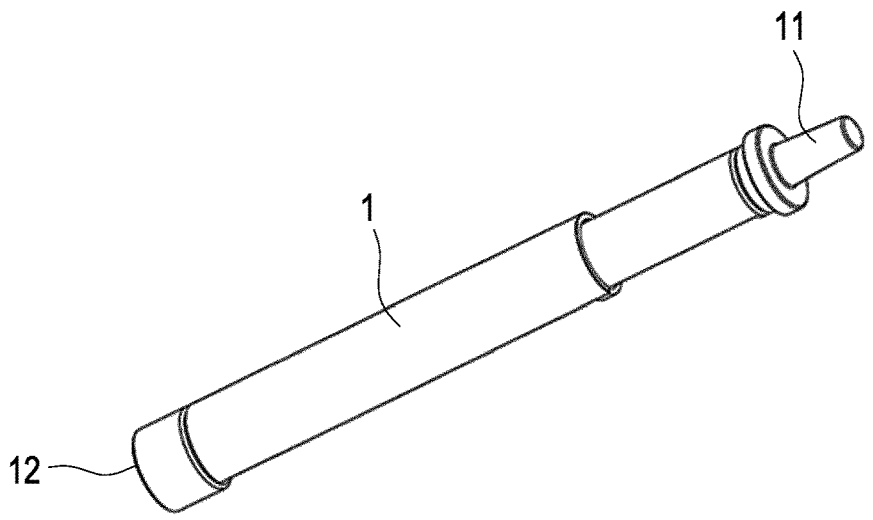
FIG. 16 is a perspective view of an implant component with an adjustment device according to an embodiment of the invention.

A system for adjusting the length of an implanted prosthesis and an adjustment device for this purpose is schematically illustrated in the form of a first embodiment in FIG. 1. A lower extremity, a leg 9, which has a bone 90 to be lengthened, in the form of a femur bone can be seen. It is divided into two parts 91, 92, wherein the implant component 1 is anchored in both parts and thus connects the two parts 91, 92 of the femur bone 90 to one another. In particular, the implant component 1 according to the invention can be a length-adjustable shaft of a prosthesis system, as is shown, for example, in FIG. 16.

For connection to other implant components, the implant component 1 according to the invention has at its two ends a respective conical connector, preferably a male cone connector 11 at one end and a female conical connector 12 at the other end (it is understood that other forms of connection are also possible, for example by means of threads, etc.). The implant component can in particular be a part of a larger joint endoprosthesis, in particular for a total replacement of the femur bone 90. By means of the adjustment device 2 (not shown in FIG. 1), the ends of the implant component 1 can be moved away from one another with the conical connectors 11, 12, i.e., the length of the implant component 1 can be changed, in particular increased.

Figure 2:
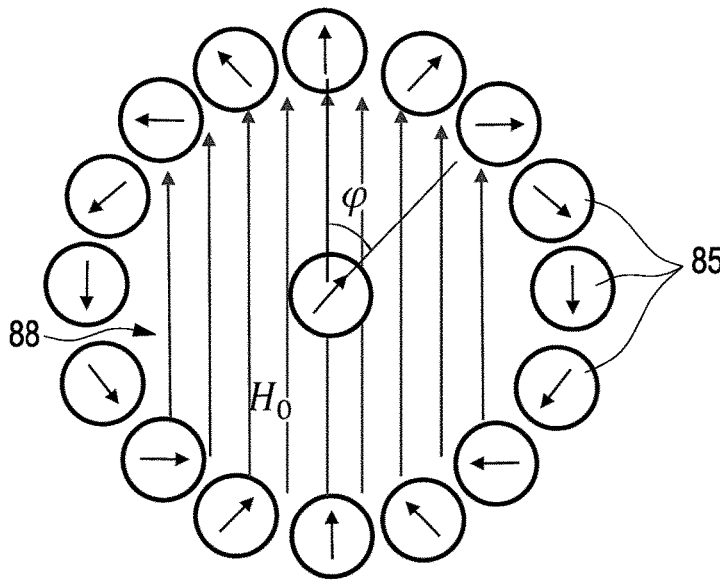
FIG. 2 is a schematic representation of a static magnetic field within a magnet ring.

An extracorporeal drive unit 7 is provided for actuating the adjustment device 2. It comprises a magnet ring 8 which is rotatably held and guided within a carrier 70. The magnet ring 8 is designed such that a directed static magnetic field is produced in its interior 80. Such a directed static magnetic field 88 is shown in FIG. 2. The magnet ring 8 here is not designed as a unitary solid body but rather is constructed discretely, namely from a plurality of sub-magnets 85. The sub-magnets 85 are each designed as a magnetic dipole, which means that the actual magnet body has a north pole "N" on the one side and a south pole "S" on the other side (this is indicated in FIG. 3a by different gray shading). If the magnet body illustrated there is developed to form a cylindrical shape, the arrangement of north pole and south pole remains basically unchanged (this is shown in FIG. 3b, wherein the direction of the remanent magnetization 87 is highlighted by a black arrow). This furthermore results in a specific magnetic orientation. In technical terms, the sub-magnets 85 are therefore dipole magnets 86 which have a directed magnetic field in the interior, as is clearly shown in FIG. 3b.

The invention makes use of this characteristic of the sub-magnets 85 and thus creates a directed static magnetic field with a manageable number (namely 16) of sub-magnets 85, which is also largely homogeneous (see FIG. 2). Here, "homogeneous" is understood to mean that a location-dependent deviation of the magnetic field strength that is not greater than +1-15% of the actual average magnetic field strength is obtained over the area of the interior 80. This is achieved by a specific angular orientation of the sub-magnets 85 in the magnet ring 8.

In this case, on the one hand, the sub-magnet 85 is arranged equidistantly to the center point, i.e., a uniform circle is ideally obtained. On the other hand, the sub-magnets 85 are inserted with different orientation into the magnet ring 8.

In order to visualize this, the direction 87 of the remanent magnetization is shown in FIG. 2 (in a corresponding manner as in FIG. 3b). It can be seen that in the center and only there, the sub-magnets 85 are each parallel to the desired course of the magnetic field lines. The further a sub-magnet 85 is inserted toward the side, the more it is inserted twisted, as can be readily derived from the position of the arrow indicating direction 87 of the magnetization. It is in particular this special twisted arrangement of the sub-magnets 85 that causes a largely homogeneous directed static magnetic field in an interior 80.

By actuating the magnet ring 8, in particular by means of a manual actuation device 75, the magnet ring 8 together with its sub-magnets 85 is brought into a rotational movement in the ring plane, as a result of which the directed static magnetic field 88 also rotates accordingly. In the simplest case, the manual actuation device 75 can be designed as a handle 75 or a handle-favorable coating of the lateral surface of the magnet ring 8, but a mechanization by means of a servo drive (not shown) may also be provided. In relation to a permanent magnet as drive element 3, the angular position of the drive of the adjustment device 2 and the currently achieved adjustment path can thus be determined easily and reliably by slowly rotating the magnet ring 8 with its static magnetic field 88. Thus, the drive unit 7 according to the invention already enables a simple but nevertheless precise control of the actual position of the permanent magnet even with the manual adjustment of the magnet ring 8 by means of the actuation element 75, from which the current angular position of the drive of the adjustment device 2 in turn results. Due to the strength of the magnetic field generated in the cavity 80 of the magnet ring 8 and the design as a static, i.e., constantly strong (albeit possibly slowly rotating) magnetic field, a slip worsening the positioning accuracy practically does not occur thanks to this arrangement. In this regard, it can be made easier for the user to detect the adjustment path achieved by optionally arranging a counting mechanism 66 on the drive unit 7, which counting mechanism monitors and indicates to the user the number of revolutions of the magnet ring 8 in the drive unit 7. Due to the precise conversion of the rotational movement of the magnet ring 8 to the permanent magnet in the drive of the implant component 1, a clear measure of the adjustment path brought about by the adjustment device 2 of the implant component 1 is thus provided.

Figure 5:
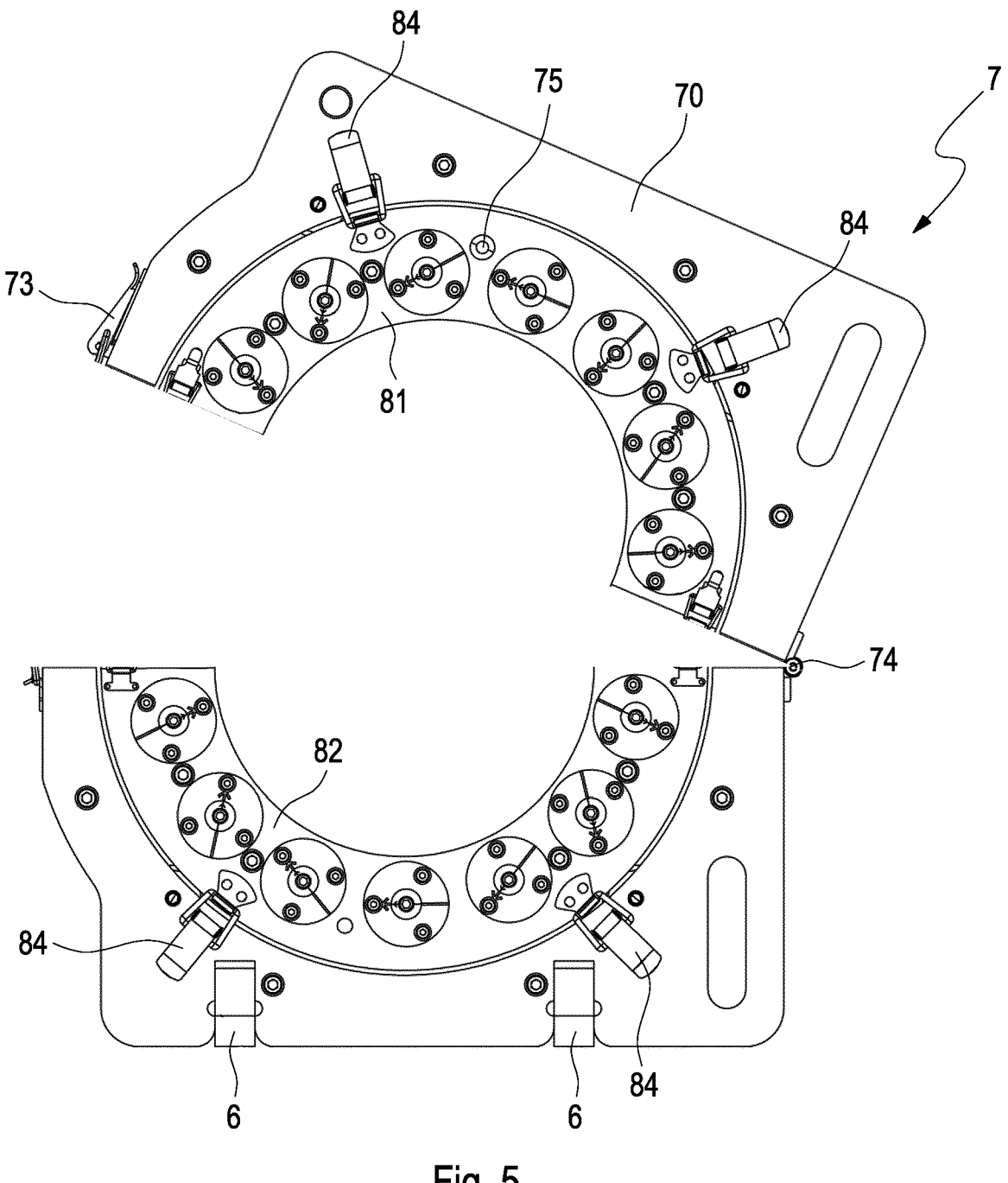
FIG. 5 is a front view of the first embodiment in a partially unfolded state.
Figure 6:
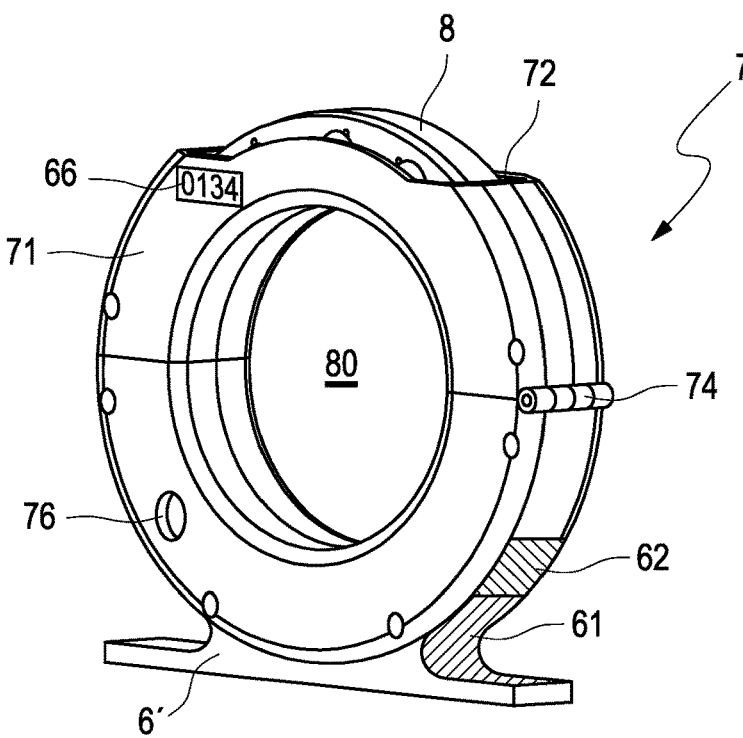
FIG. 6 is a perspective view of a second embodiment of a drive unit according to the present invention.

An example of a structural design of the drive unit 7 comprising a magnet ring 8 is explained below with reference to FIGS. 4 and 5 on the basis of a first exemplary embodiment. The drive unit provided in its entirety with the reference sign 7 comprises a carrier 70 in which the magnet ring 8 is rotatably mounted. Here, the inner side of the circular recess acts as a guide 78 for the magnet ring 8. Furthermore, two engagements 75', which are provided as handles for carrying, are formed in the carrier 70. They enable problem-free movement and positioning of the drive unit 7. Two supporting feet 6 are provided in the lower region of the drive unit 7. They serve to hold the drive unit 7 in an erected position in a tilt-protected manner so that the extremity (leg 9) can be guided with the implant component 1 through the interior 80 of the magnet ring 8.

The magnet ring 8 is divided into two segments 81, 82, which are each designed as a semi-circular arc. The outer circumference of the magnet ring 8 is mounted in the carrier 70 by way of a circular recess, which is shaped complementarily on an inner side.

The carrier 70 is divided into an upper and a lower half along a horizontally extending dividing line. For this dividing line, a buckle closure 73 is provided on a lateral side of the carrier 70 and a hinge 74 is provided on its opposite lateral side. By opening the buckle closure 73, the upper half of the carrier 70 can be unfolded upward, namely with the hinge 74 as a pivot point. When unfolding, the segment 81 of the magnet ring 8 remains on the upper half and the segment 82 of the magnet ring 8 remains on the lower half of the carrier 70. In order to avoid falling out or twisting of the segments 81, 82, a total of four locking closures 84, two for each of the segments 81, 82, are provided for locking the magnet ring 8 on the carrier 70. In the closed state, the two segments 81, 82 are connected to one another by clamping closures 83'. If they are closed, the two segments 81 and 82 form the uniform magnet ring 8.

The magnet ring 8 comprises a plurality (14 in the illustrated exemplary embodiments) of cylindrical sub-magnets 85 made of rare earth material. Suitable receptacles on the magnet ring 8 are provided for holding said sub-magnets on the magnet ring 8. The cylindrical sub-magnets 85 are inserted into said receptacles and are fastened in a torsion-proof manner and secured from falling out. The anti-torsion lock is significant since the individual sub-magnets 85 are inserted and held with exactly defined angular orientation. The angular orientation is used for a specific alignment of the magnetic field generated by the respective sub-magnet 85 and is visualized by arrows in FIGS. 4 and 5 (cf. for the significance of the arrows also the above explanation of FIGS. 2 and 3b). It can be seen that the angular orientation of the individual sub-magnets 85 is always different from the adjacent ones. The orientation is selected methodically in such a way that the magnetic field is concentrated on the interior 80 (the exterior space of the magnet ring 8 is substantially field-free), and a substantially homogeneous, directed static magnetic field thus arises in the interior 80 (cf. FIG. 2 and the above explanation in this respect).

By rotating the magnet ring 8, in particular manually, the static magnetic field 88 produced in this way can be rotated, wherein a permanent magnet located in the interior 80 rotates synchronously under the action of the magnetic field. Such a permanent magnet is used as a drive element for the implant component, as explained below.

A second embodiment for a drive unit 7' is shown in FIGS. 6 to 11. It differs in terms of its shape design but is functionally substantially similar to the first embodiment described above. The same reference signs are used for the same or similar parts, with reference being made to the above explanation in order to avoid unnecessary repetition, which explanation is to be applied analogously.

The second embodiment of the drive unit 7' has, instead of the carrier 70, a housing 71 surrounding the magnet ring. It surrounds the magnet ring 8 substantially completely, with the exception of a large opening 72 in the upper region of the housing 71. Said opening is dimensioned so as to enable an access extending over at least 30°, thus a twelfth of the circumference of the magnet ring 8, so that the user can manually rotate the magnet ring 8, in particular on the lateral surface of the magnet ring 8 which is designed for manual actuation (provided with grip coating). It should be noted that a manual drive is not imperative, however. A coupling opening 76 in the housing 71 is provided for a possible flanging of a drive motor. Here, a drive motor (not shown) can be arranged which acts on the magnet ring 8 and sets it in rotation. It should be noted that such a motorized drive may optionally also be provided in the first embodiment.

The housing 71 is preferably made of soft magnetic material, for example highly permeable iron, nickel and/or cobalt alloys, in order to thus shield the exterior space from the magnetic (residual) field of the magnet ring 8. In particular, low-alloy construction and machining steels or electrical steel sheets are expedient.

Preferably, at least the housing 71 is designed to shield in the region of the lateral surface of the magnet ring 8. Expediently, the housing 71 in this case is dimensioned in such a way that it has a distance from the magnet ring 8 in the region of the shield (e.g., lateral surface), which distance is at least as large as the diameter/height of the individual sub-magnets 85, preferably a multiple thereof. A good shielding effect can thus also be achieved with relatively low material thicknesses (typically 0.5 mm or less) and thus little weight. If, optionally, a shielding is also to be brought about in the region of the end faces of the magnet ring 8, either the housing 71 would be designed with a quite large depth in order to achieve the aforementioned distance of the end-face housing wall of at least the diameter/height of the individual sub-magnets 85, or the material thickness of the end-face housing wall would be considerably higher than in the region of the lateral surface, usually more than twice or even three times as thick (i.e., typically greater than 1 mm).

The housing 71 is furthermore provided with a direction-oriented receptacle for an extremity, for example a leg. However, the extremity provided with the implant component 1 should not be received here, but rather its contralateral counterpart, i.e., the other leg. For this purpose, as shown by way of example in FIG. 6, the housing 71 is provided in the region of its supporting foot 6' with a recess which is substantially V-shaped in cross-section and forms a receptacle 61. In the embodiment shown, it is dimensioned such that the lower leg of the other leg (not shown) can be received in the region of the receptacle 61 or alternatively/additionally is dimensioned so much larger that the thigh of the other leg (not shown) can be received in the region of the receptacle 62. The receptacle 61, 62 is expediently shaped such that it receives the extremity only in a defined position. Accordingly, if the lower leg or thigh of said other leg is placed in the receptacle 61, 62, the drive unit 7' is, so to speak, automatically aligned correctly for adjusting the implant component 1 to be set (for other extremities, such as arms, this applies accordingly). This simplifies the correct application or positioning of the drive unit 7' according to the invention for the user. It should be noted that the receptacles 61, 62 can also be designed as individually adapted forms.

Figure 7:
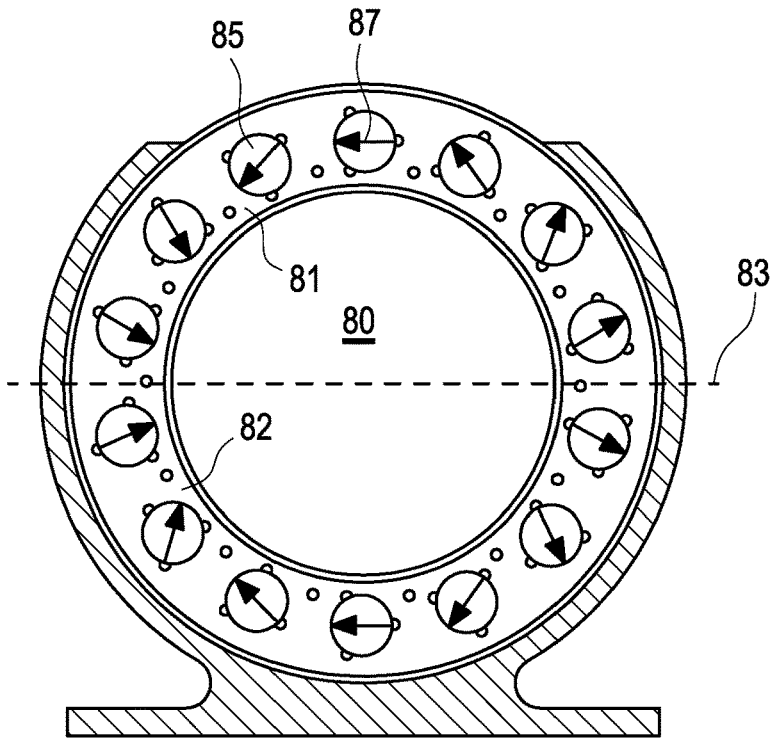
FIG. 7 is a sectional view of the second embodiment with a section through the housing and front view on the magnet ring.
Figure 8:
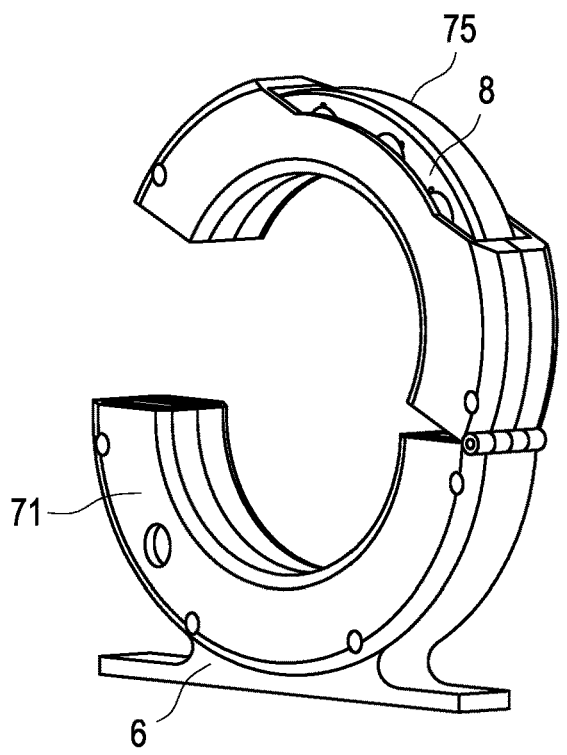
FIG. 8 is a perspective view of the second embodiment in a partially unfolded state.
Figure 9:
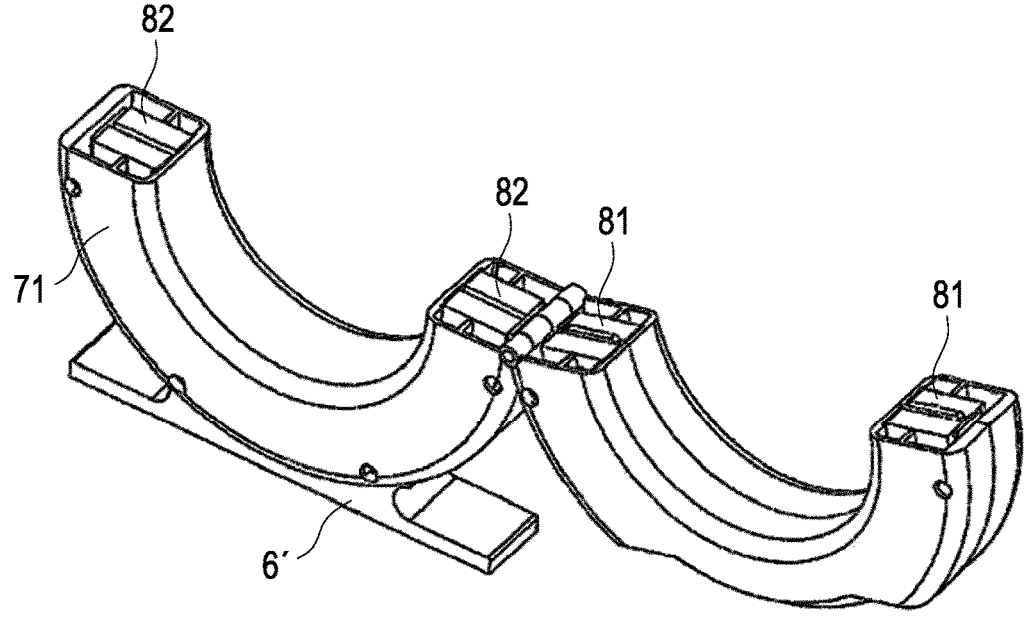
FIG. 9 is a perspective view of the second embodiment in a fully unfolded state.

As also in the first embodiment, the magnet ring 8 is provided with a plurality of sub-magnets 85, which are shown in the partial sectional representation in FIG. 7. Here again, the alignment of the sub-magnets 85 visualized by the arrows 87 in order to form the concentrated directed static magnetic field according to the invention in the interior 80 can be seen. Here too, the magnet ring 8 is again subdivided into two segments 81, 82, which can be unfolded together with the upper half of the housing 71 (see FIGS. 8 and 9). As in the first embodiment, a hinge 74 is provided for this purpose on one side. FIG. 9 shows the second embodiment with completely unfolded housing 71. The respective ends of the segments 81, 82, which lie in the separation plane 83 in the folded state (see FIG. 7), can be clearly seen at the separation surfaces.

Figure 10:
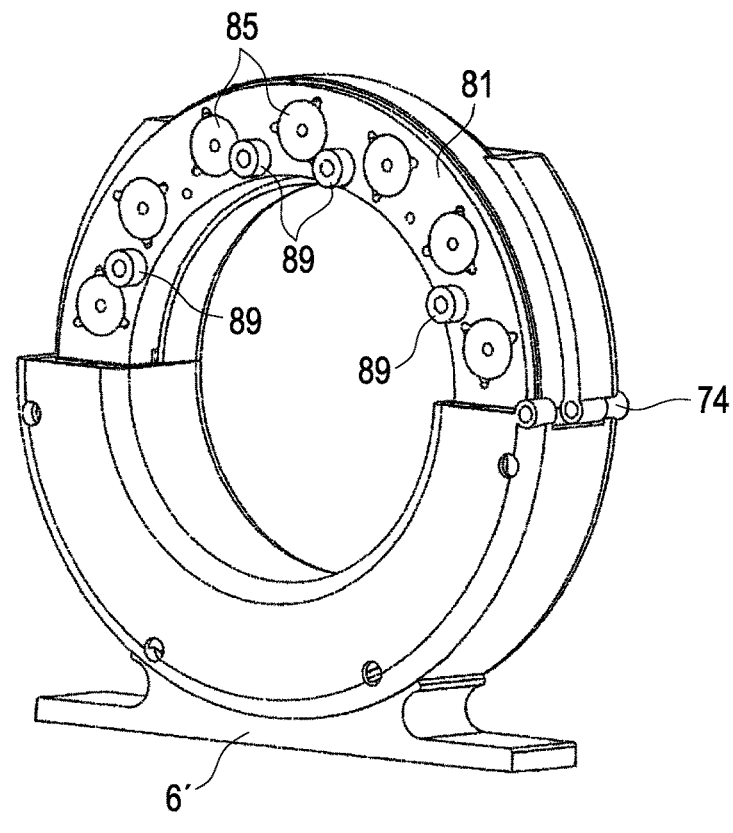
FIG. 10 is a perspective view of the second embodiment with partially removed housing upper part.
Figure 11:
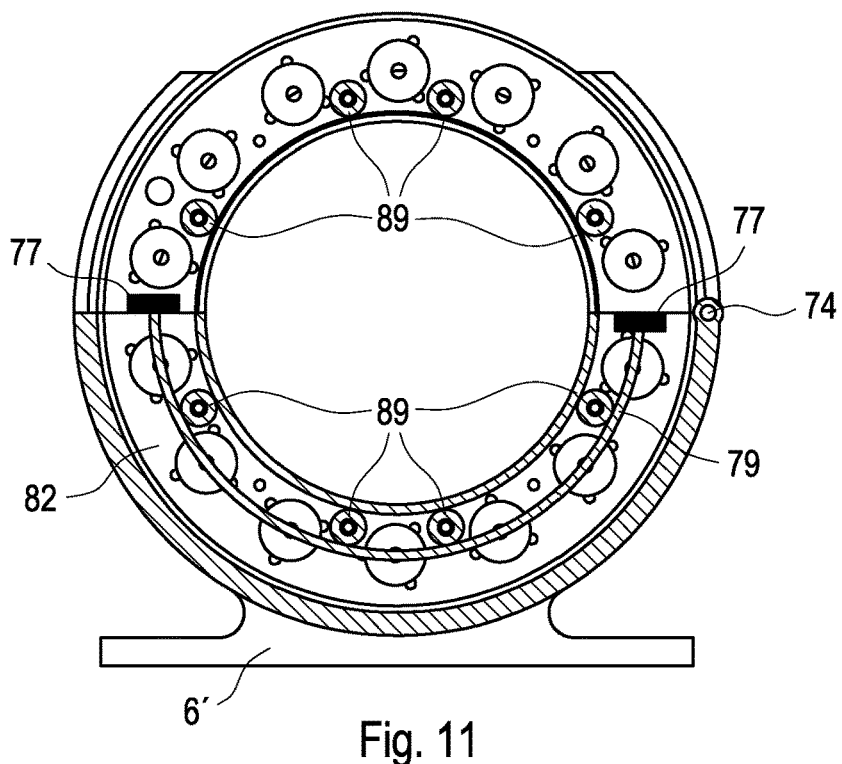
FIG. 11 is a front view as a section through the housing of the embodiment shown in FIG. 10.

In the representation shown in FIG. 10, a part of the upper region of the housing 71 is removed. In addition to the upper segment 81 of the magnet ring 8, the sub-magnets 85 thereof can be seen clearly, as described above. Furthermore, a plurality of guide rollers 89 can be seen on the magnet ring 8, which guide rollers interact with a curved guide rail 79 arranged in the lower region of the housing 71 (see FIG. 11). In this way, a secure positive guidance of the magnet ring 8 in the housing 71 is achieved. It is sufficient that the curved guide rails 79 extend over the lower housing half since, thanks to the connection of the segments 81, 82 in the folded normal state, a complete guidance of the magnet ring 8 results in this way. In the unfolded state, this does not apply to the upper segment 81, but the latter is secured by virtue of its curved shape and a locking bolt 84' in the likewise curved upper half of the housing 71 to the extent that it cannot fall out. When the housing 71 is folded and the segments 81, 82 are subsequently mutually locked, the magnet ring 8 is closed again, and the drive device 7' is then ready for use again without further intervention.

Figure 12:
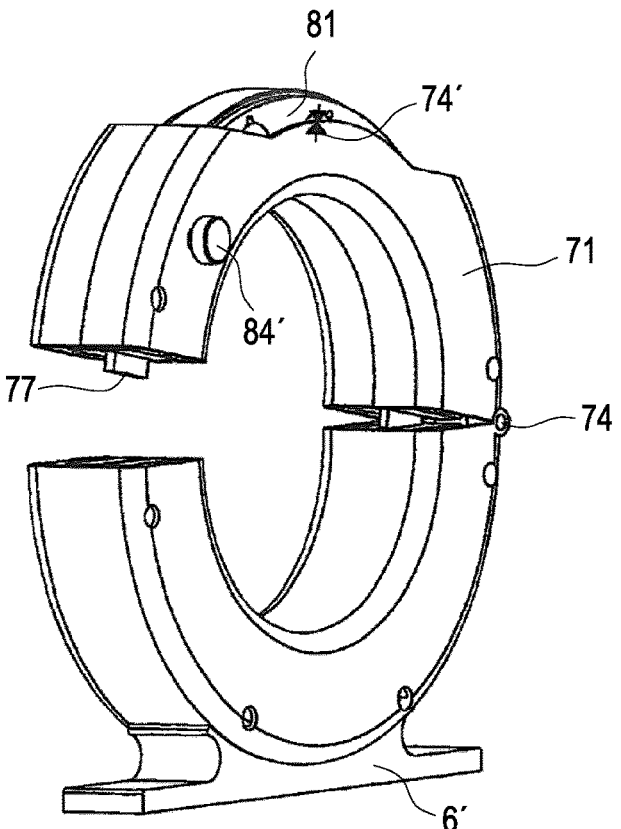
FIGS. 12a, b are further perspective views of the second embodiment with the upper housing part placed thereon and with a partially sectioned lock.
Figure 12:
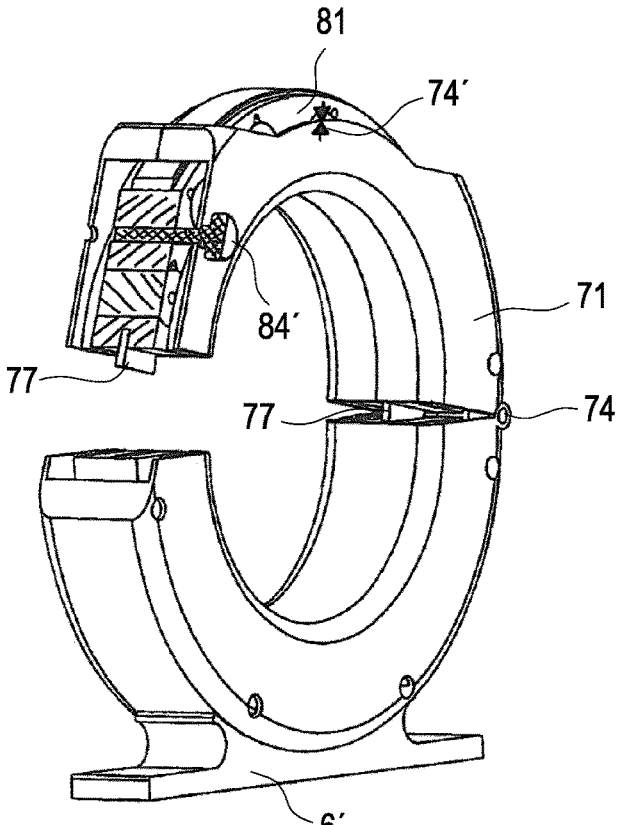

In order to ensure a correct relative positioning of the two segments 81, 82 in the closed (folded) state, guide elements 77 are provided. They are designed in the manner of a pawl and are arranged at the two ends of the guide rail 79 in the region of the separation plane 83 on the segments 81, 82 (see FIGS. 12 and 13). They are part of a spring catch mechanism which holds the segments 81, 82 together. In the closed state, this results in effective guidance and securing for the magnet ring 8, namely by means of the guide rollers 89 guided on the guide rail 79 and the guide elements 77 at the ends of the guide rail 79.

For locking in the secured position, a locking bolt 84' is provided, which can be plugged into corresponding receiving openings in the upper region of the housing 71 and in the upper segment 81 of the magnet ring 8 (see FIGS. 12*a, b*).

The position in which the magnet ring 8 has to stand for inserting the locking bolt 84' is that in which the separation plane 83 between the segments 81, 82 is aligned with the hinge 74 of the housing 71; only in this basic position is unfolding possible. The correct position of the magnet ring 8 in this basic position is indicated by a reference mark 74' arranged in the region of the housing opening 72, one half of said mark being attached to the housing 71 and the other half of said mark being attached to the magnet ring 8 (for example as double arrow mark); if they are lined up over one another, the basic position is reached.

In this basic position, the receiving openings are aligned in the housing 71 and segment 81 of the magnet ring 8, and the locking bolt 84' can be inserted. This results in a positive guidance, by means of which the magnet ring 8 is locked, wherein at the same time, the spring catch mechanism is unlocked by means of a mechanical combination so that the segments 81, 82 are decoupled and the magnet ring 8 can be unfolded. As a result of the locking bolt 84', the upper segment 81 of the magnet ring 8 is here also secured against undesired movement during the unfolding or in the unfolded state.

A third embodiment for a drive unit 7" is shown in FIGS. 13*a, b* and 14. It is based on the second embodiment but, in contrast thereto, has a differently designed housing 71. In the upper region, it has an outer protective cover 72' which is mounted in a foldable manner on the hinge 74 and exposes the upper region of the magnet ring 8 in the open state. A cantilever 71" is provided on the housing 71 in the region of the hinge 74. On the one hand, it carries the handle 75' for the transport of the drive unit 7" and, on the other hand, forms a stop for the protective cover 72' in this way in order to thus achieve an opening limitation.

The cantilever 71" is furthermore shaped such that with its side contour, it offers a receptacle 61 for the contralateral extremity (the other leg). Otherwise, its functionality corresponds to that of the receptacle 61 in the second embodiment so that reference is made thereto to avoid repetitions. This also applies accordingly to the other components of the third embodiment, which carry the same or corresponding reference signs as the corresponding components of the second embodiment.

As a special feature, the third embodiment furthermore has a counterpart to the outer protective cover 72'. An inner protective cover 71', which separates the interior 80 from the magnet ring 8, is provided on the inside of the magnet ring 8. It acts not only as a mechanical cover but also serves to shield the surrounding region, in particular adjacent regions of the extremity to be received (in particular leg 9), against unnecessary load through magnetic fields.

The magnet ring 8 is mounted on guide rollers 89' which are arranged fixedly on the housing and on which the magnet ring 8 rests in its lower region with its lateral surface. This allows a compact construction with a relatively low center of gravity. The risk of unintentional tipping of the drive unit 7" can thus be counteracted. Optionally, the guide rollers 89' are designed at their end faces with an enlarged diameter so that a collar is produced and a lateral guide for the magnet ring 8 is achieved. Additional guide rollers 89' can also be provided in particular in the upper region of the housing.

Furthermore, in this third embodiment, the housing 71 has double-formed supporting feet 6". They give the drive unit 7" a wider contact area and thus further increase safety against tipping. Moreover, in order to avoid repetitions, reference is made to the above description of the second embodiment.

Figure 15:
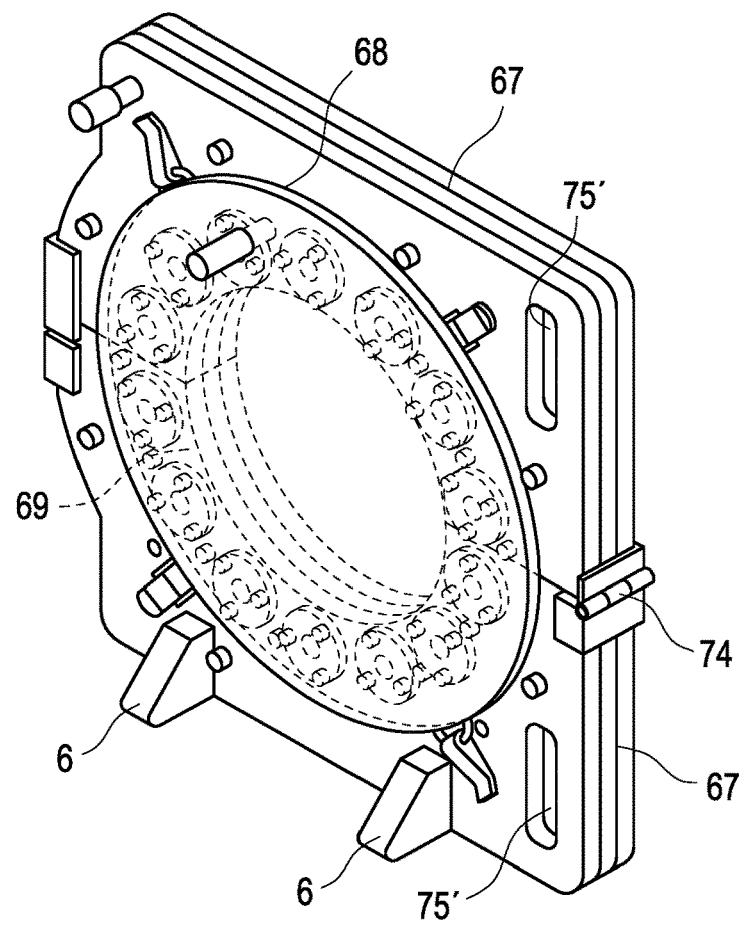
FIG. 15 shows representations for shielding using the example of the first embodiment.

Magnetic shields, preferably made of magnetically highly conductive (highly permeable) material, in particular soft magnetic (ferromagnetic) materials, such as iron, nickel and cobalt alloys, can be provided on the magnet ring 8 or the surrounding housing 71 and its components 71', 72'. For the sake of clarity, various shields are explained below with reference to FIG. 15 with respect to the first embodiment, wherein the same applies accordingly to the other embodiments. An outer shield 67 can be provided at a relatively large distance, which is understood to mean a multiple of the diameter or the height of the sub-magnets 85. With such a spaced-apart shielding, material thicknesses of the shielding material of only a few tenths of a millimeter are sufficient and advantageous.

A directly adjacent jacket shielding 68 is expediently provided for shielding on the magnet wheel 8. Typically, the distance of the shielding is here approximately equal to the diameter or the height of the sub-magnets 85 so that material thicknesses of at least half a millimeter, preferably up to one millimeter, are expedient. Such a jacket shielding can also be expedient on the inside, for example on the inner protective cover 71' of the third embodiment for the protection of surrounding regions of the relevant leg 9.

Furthermore, shielding can also be provided as a near-field shield 69 on the end faces of the magnet wheel. The distance here is typically smaller than the diameter or the height of the sub-magnets 85 so that a strong magnetic control of the soft iron occurs. Rather large material thicknesses of at least one, usually several millimeters are therefore required.

Figures 17, 18, 19:
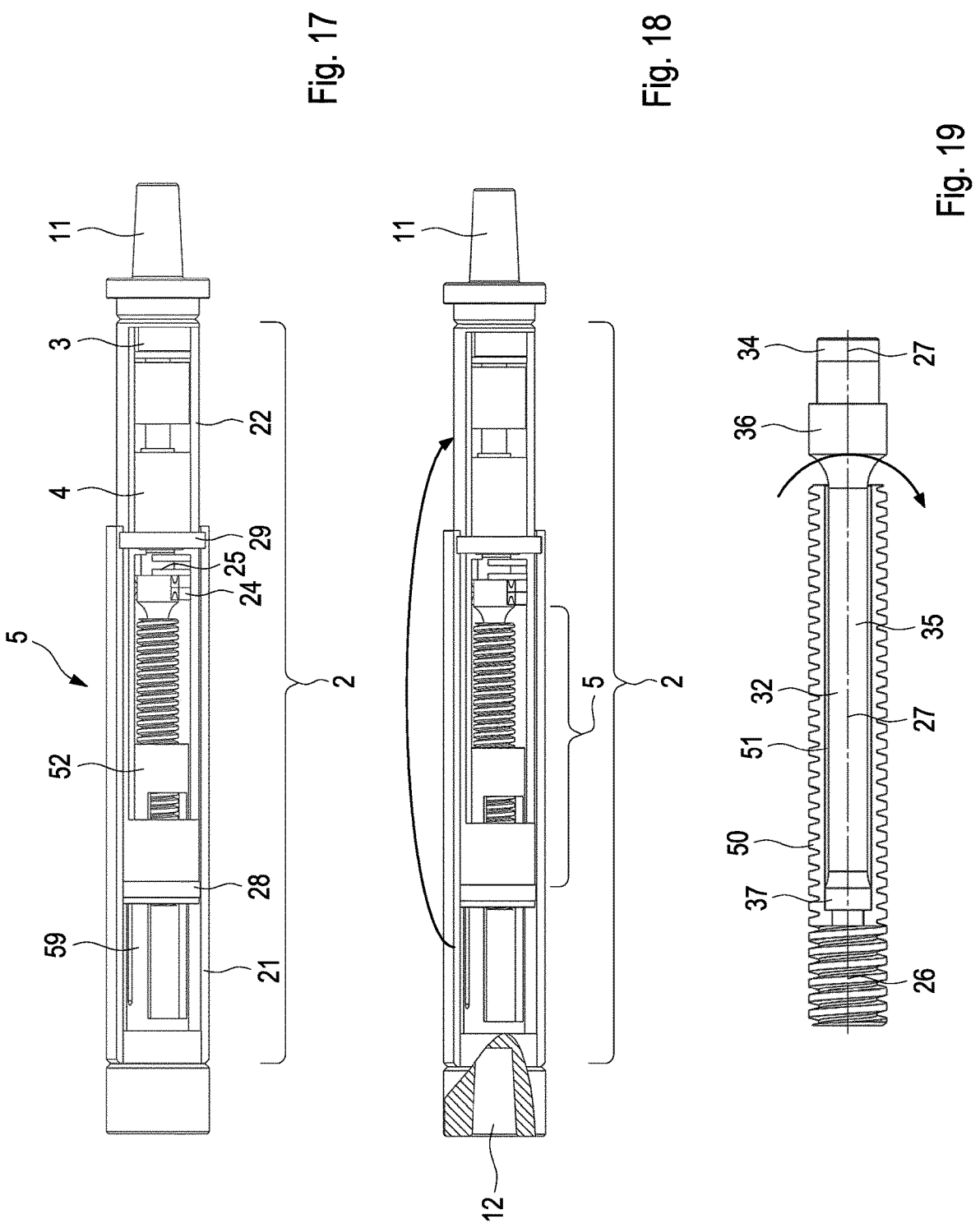
FIG. 17 is a plan view of the implant component with an exposed interior.
FIG. 18 is a partially sectioned representation of the implant component according to FIG. 17.
FIG. 19 is a sectional view of a spindle for an adjustment device of the implant component.

An exemplary embodiment for an implant component 1 is shown in FIGS. 17 to 19. FIG. 17 shows a partial section through the implant component 1 with its adjustment device 2. In the exemplary embodiment shown, the implant component 1 is shaped like a shaft and thus forms part of a prosthesis shaft, in particular for a modular prosthesis system.

At each of its two ends, it has a coupling element on adjacent prosthesis modules of a preferably standardized prosthesis system, for example a further shaft or a connection to a joint component. The implant component 1 thus has a male cone 11 as a coupling element at its end shown on the right in FIG. 17 and a coupling element designed as a female cone 12 at its end shown on the left in the representation for connecting further prosthesis modules (not shown); it is understood that connection types other than conical connectors can also be provided.

The actual shaft body between the coupling elements 11, 12 is designed with an outer tube 21 and an inner tube 22 guided longitudinally displaceably therein. They are part of an adjustment device 2 and interact telescopically in order to enable the adjustment of different lengths for the implant component 1. The outer tube 21 and the inner tube 22 are connected to one another via two sliding guides, of which one sliding guide 28 is arranged at the free end of the inner tube 22 and movably in the outer tube 21, while the other sliding guide 29 is fixedly arranged at the end of the outer tube 21 in the region of the transition to the inner tube 22. Furthermore, a guide groove is arranged on the inner side of the outer tube 21 in order to avoid mutual twisting of the inner tube 22 in relation to the outer tube 21. An axial bearing 25, which is likewise arranged at the end of the outer tube 21 and to which a sealing ring pair 24 is assigned, serves as bearing for longitudinal adjustment in order to close the interior of the outer tube 21 in relation to surrounding body tissue or fluids.

The adjustment device 2 for adjusting the length of the implant component 1 furthermore comprises a drive element 3 which has a permanent magnet arranged rotationally movably about a central axis of the inner tube. It is designed with such an alignment that its polarization direction (direction from the north pole to the south pole) is orthogonal to the central axis. Expediently, a sub-magnet 85, as described above, is also used for this purpose. Arranged downstream of the drive element 3 is a gearing mechanism 4 as a reduction gear. In the illustrated exemplary embodiment, it is designed as a two-stage planetary gear which has a reduction of approximately 1 to 20.

The gearing mechanism 4 acts on a spindle drive 5, which converts a rotational movement of the gearing mechanism 4 into a linear movement for longitudinal adjustment. A bending beam 35 is provided for transmitting torque between gearing mechanism 4 and spindle drive 5. The gearing mechanism 4 acts on a driven end 34 of the bending beam 35, which is arranged coaxially to the central axis 27 of the inner tube 22. The bending beam 35 furthermore has a collar 36, which is arranged in the region of the sealing rings 24, and has, adjoining thereto, an elongated constricted shaft region 32 which ends at a coupling piece 37 at the free end of the bending beam 35. The elongated constricted shaft region 32 is inserted into a central bore 51 of the drive spindle 50 that is open on one side, wherein the coupling piece 37 is connected to the drive spindle 50 at the bottom of the central bore 51. The drive spindle 50, which is set in rotary motion by the bending beam 35, rotates about a central axis 26 of the outer tube 21 and thus brings about a longitudinal movement of an adjustment slide 52 which is arranged on the drive spindle 50 and is fixedly connected to the inner tube 22. A rotation of the drive magnet 3 thus ultimately brings about, via the reduction gear 4 and the spindle drive 5, a longitudinal adjustment of the implant component 1.

Reference is now made to FIGS. 18 and 19. During operation, bending stress occurs in the adjustment device 2 under load. A substantial load resulting from the longitudinal adjustment of the implant component 1 is a buckling load, which stresses the substantially shaft-like implant component 1 on bending. This stress is symbolized by an elongated arrow in FIG. 18. As a result of this stress, angle errors can arise between the central axis 26 of the outer tube 21 and the central axis 27 of the inner tube 22, i.e., under load, the two central axes 26, 27 no longer align but have an angular misalignment of a few degrees.

The sensitive torque transmission from the drive magnet 3 to the spindle drive 5 can thereby be considerably disturbed, as a result of which undesired blocking can occur. According to the invention, the bending beam 35, which can absorb the misalignment thanks to its bending (symbolized by the arrow representation in FIG. 19), provides a remedy here. It enables the compensation of misalignments in the range of up to +/−5 degrees, preferably up to +/−2 degrees. It thus increases the tolerance of the drive train to bending stress and thus increases the load-bearing capacity and reliability of the adjustment device 2 of the implant component 1.

The implant component 1 with its adjustment device 2 is adjusted by placing the extremity (leg 9) with the implant component 1 in the interior 80 of the drive unit 7, 7' such that the adjustment device 2 with its drive magnet 3 lies in the plane of the magnet ring 8. By actuating the drive unit 7, 7', specifically in that the magnet ring 8 is generally rotated by hand, the magnetic field 88 co-rotating synchronously with the magnet ring 8 acts on the drive magnet 3, which is then likewise rotated synchronously therewith in a corresponding manner. By means of the static magnetic field, which is not modulated with respect to its strength in contrast to a typical electromagnetically generated field (in particular an electric motor winding) but has a constant strength, slip between the drive magnet 3 and the magnet ring 8 is reliably avoided. The angular position as well as the number of revolutions of the magnet ring 8 is thus equal to that of the drive magnet 3. Precise longitudinal adjustment can thus be carried out in a simple manner. The number of rotations performed for adjustment (and thus the adjustment path achieved in this way) is here indicated for the user on the counting mechanism 66.

The invention claimed is:

1. An extracorporeally length-adjustable implant system comprising an implant component for an implantable prosthesis for attachment to a bone to be lengthened having an adjustment device comprising two fastening parts that are displaceable relative to one another, each of which is to be arranged on a part of the bone to be lengthened, wherein the adjustment device is designed to displace the two fastening parts, and comprises a drive element comprising a permanent magnet arranged rotationally movably, and a gearing mechanism to convert the rotational movement of the permanent magnet into a displaceable longitudinal movement of the adjustment device; and an extracorporeal drive unit for the drive element of the implant component, wherein the extracorporeal drive unit comprises a rotatably mounted extracorporeal magnet ring having an interior which is designed to receive the bone to be lengthened with the adjustment device, and an actuation device which is designed to rotate the extracorporeal magnet ring in its ring plane, wherein the extracorporeal magnet ring is designed as a permanent magnet structure and has, in its interior, a static magnetic field, which is stationary with respect to the ring, and the extracorporeal magnet ring is mechanically rotatable by the actuation device, wherein the magnet ring can be divided into at least two segments creating an openable and closable access for a body part provided with the implant component to the interior of the magnet ring, wherein the segments can be unfolded into an open position of the magnet ring.

2. The implant system according to claim 1, wherein the magnetic field is concentrated on the interior.

3. The implant system according to claim 1, wherein the directed static magnetic field is unidirectional and homogeneous in the central interior.

4. The implant system according to claim 1, wherein the segments can be unfolded, without magnetic force, into an open position of the magnet ring.

5. The implant system according to claim 1, wherein a separation plane between the segments is selected such that it extends in parallel to the directed static magnetic field.

6. The implant system according to claim 1, wherein the segments are such that at least one is openable and reclosable and at least one is foldable in a hinge-like manner.

7. The implant system according to claim 1, wherein a locking device is provided which fixes the magnet ring with its segments in a rotationally secure manner in an open position.

8. The implant system according to claim 1, wherein a securing device is provided on the magnet ring having a locking bolt to block an unfolding of the magnet ring outside of the open position.

9. The implant system according to claim 1, wherein the magnet ring is formed by a plurality of similar sub-magnets.

10. The implant system according to claim 9, wherein the sub-magnets are similar magnetic dipole bodies.

11. An extracorporeally length-adjustable implant system comprising an implant component for an implantable prosthesis for attachment to a bone to be lengthened having an adjustment device comprising two fastening parts that are displaceable relative to one another, each of which is to be arranged on a part of the bone to be lengthened, wherein the adjustment device is designed to displace the two fastening parts, and comprises a drive element comprising a permanent magnet arranged rotationally movably, and a gearing mechanism to convert the rotational movement of the permanent magnet into a displaceable longitudinal movement of the adjustment device; and an extracorporeal drive unit for the drive element of the implant component, wherein the extracorporeal drive unit comprises a rotatably mounted extracorporeal magnet ring having an interior which is designed to receive the bone to be lengthened with the adjustment device, and an actuation device which is designed to rotate the extracorporeal magnet ring in its ring plane, wherein the extracorporeal magnet ring is designed as a permanent magnet structure and has, in its interior, a static magnetic field, which is stationary with respect to the ring, and the extracorporeal magnet ring is mechanically rotatable by the actuation device, wherein the magnet ring is formed by a plurality of similar sub-magnets, wherein the sub-magnets are regularly inserted along the magnet ring in an angularly fixed manner with different orientation of the magnetization.

12. The implant system according to claim 11, wherein the sub-magnets are arranged such that their magnetic stray field is maximally compensated along a separation plane between segments of the magnet ring in each case.

13. The implant system according to claim 12, wherein the sub-magnets are arranged such that their magnetic stray field is equal to zero along a separation plane between segments of the magnet ring.

14. The implant system according to claim 1, wherein a housing for the drive unit is provided, said housing is provided with one or more shields and surrounding the magnet ring.

15. The implant system according to claim 1, wherein the drive unit is provided with a positioning device which acts on the magnet ring.

16. The implant system according to claim 1, wherein the drive unit is provided with a supporting foot provided with a direction-oriented receptacle for a body part.

17. The implant system according to claim 1, wherein the adjustment device of the implant component further comprises a spindle drive which is actuated by the drive element via the gearing mechanism to convert the rotational movement of the permanent magnet into a displaceable longitudinal movement.

18. An implant component comprising an adjustment device for an implantable prosthesis designed for fastening to a bone to be lengthened, comprising two fastening parts that are displaceable relative to one another and are displaced relative to one another by the adjustment device for longitudinal expansion, wherein the adjustment device comprises a drive element comprising a permanent magnet which is arranged rotationally movably and acts via a gearing mechanism on a spindle drive to convert a rotational movement of the permanent magnet into a displaceable longitudinal movement, wherein the drive element is designed for actuation by means of a magnetic field of an extracorporeal drive unit, wherein a bending beam is provided for transmitting force from the drive element to the spindle drive.

19. The implant component comprising an adjustment device according to claim 18, wherein a spindle of the spindle drive has a central bore which is open on one side and into which the bending beam is inserted.

\* \* \* \* \*